United States Patent [19]
Cope et al.

[11] Patent Number: 5,514,656
[45] Date of Patent: May 7, 1996

[54] METHOD OF PROVIDING ENTERAL NUTRITIONAL SUPPORT FOR PATIENTS UNDERGOING RADIATION THERAPY AND/OR CHEMOTHERAPY

[75] Inventors: Frederick O. Cope, Worthington; Normanella T. DeWille, Upper Arlington; Ernest W. Richards, Columbus; Terrence B. Mazer, Reynoldsburg; Bonnie C. Abbruzzese, Dublin; Gregory A. Snowden, Pickerington; Nickki L. Parlet; Laura A. Pease, both of Columbus, all of Ohio

[73] Assignee: Abbott Laboratories, Abbott Park, Ill.

[21] Appl. No.: 68,450

[22] Filed: May 28, 1993

[51] Int. Cl.$^6$ .............................. A23J 3/16; A23L 1/052; A61K 38/17; A61K 47/42
[52] U.S. Cl. ................................ 514/21; 514/2; 426/654; 426/656; 426/657
[58] Field of Search .................... 514/2, 21; 426/654, 426/656, 657

[56] References Cited

U.S. PATENT DOCUMENTS

| | | | |
|---|---|---|---|
| 4,100,024 | 7/1978 | Adler-Nissen | 195/29 |
| 4,920,098 | 4/1990 | Cotter et al. | 514/2 |
| 4,959,350 | 9/1990 | Frokjaer et al. | 514/2 |
| 5,053,387 | 10/1991 | Alexander | 514/2 |
| 5,108,767 | 4/1992 | Mulchandini et al. | 514/2 |
| 5,221,668 | 6/1993 | Henningfield et al. | 514/2 |
| 5,223,285 | 6/1993 | DeMichele et al. | 426/72 |
| 5,308,832 | 5/1994 | Garleb et al. | 514/2 |

FOREIGN PATENT DOCUMENTS

| | | |
|---|---|---|
| 0246747 | 11/1989 | European Pat. Off. . |
| 59-045854 | 8/1984 | Japan . |
| 60-251840 | 12/1985 | Japan . |
| WO91/13554 | 9/1991 | WIPO . |
| 9218015 | 4/1992 | WIPO . |

OTHER PUBLICATIONS

Swenson et al Metabolism, vol. 40, No. 5 (May) 1991, pp. 484–490.
Newberne et al Recent Prog. in Res. on Nutrition and Cancer, pp. 119–134 (1990).
Food Chemistry Second Edition, Revised and Expanded, edited by O. Fennema, Marcel Dekker, Inc., (1985), pp. 246–247, 282–283, 817.
Bounous et al., "Elemental Diet in the Management of the Intestinal Lesion Produced by 5–Fluorouracil in Man", The Canadian Journal of Surgery, 14:312–324 (1971).
Hugon et al., "Elemental Diet in the Management of the Intestinal Lesions Produced by Radiation in the Mouse", The Canadian Journal of Surgery, 15:18–26 (1972).
Haddad et al., "Long–Term Nutrition with an Elemental Diet Following Intensive Abdominal Irradiation: Report of a Case", Diseases of the Colon and Rectum, 17(3):373–375 (1974).
Bounous et al., "Dietary protection during radiation therapy", Strhlentherapie, 149(5):476–483 (1975).
Bounous et al., "The Use of Elemental Diets During Cancer Therapy", Anticancer Research, 3:299–304 (1983).
McCardle et al., "Elemental Diet as Prophylaxis Against Radiation Injury", Archives of Surgery, 120:1026–1033 (1985).
McCardle et al., "Prophylaxis Against Radiation Injury", Archives of Surgery, 121:879–884 (1986).
Coulston et al., "Nutrition management of patients with cancer", Topics in Clinical Nutrition, 12:26–36 (1986).
Kouba, "Nutritional Care of the Individual with Cancer", Nutrition in Clinical Practice, 3:175–182 (1988).
Shou et al., "Dietary Manipulation of Methotrexate–Induced Enterocolitis", Journal of Parenteral and Enteral Nutrition, 15(3):307–312 (1991).
"Enteral Peptide Formulas Inhibit Radiation Induced Enteritis and Apoptosis in Intestinal Epithelial Cells and Suppress the Expression and Function of Alzheimer's and Cell Division Control Gene Products", Cope et al., The FASEB Journal, p. A931, Mar. 15, 1991.
"Induction of Expression of the Alzheimer's Gene by Radiation in Intestinal Epithelial Cells; Implications for a Novel Paradigm in Gene–Directed Cell Death (Apoptosis)", Tomei et al., The FASEB Journal, p. 1606, Mar. 19, 1991.
"Inhibition of the Intestinal Expression of the Alzheimer's and Cell Division Control Gene Product and Functions by Enteral Peptides Marks the Inhibition of Radiotherapy Induced Enteritis and Apoptosis", Cope et al., Abstract #48, Proceedings of the 82nd Annual Meeting of the American Assoc. for Cancer Research, (1991).
"Prophylactic Enterotrophic Peptide Inhibition of Radiotherapy Induced Enteritis is Marked by Down Regulation of the Expression of the Amyloid Beta Protein, CK II and Apoptosis", Cope et al., Abstract #1537, Proceedings of the 83rd Annual Meeting of the American Association for Cancer Research (1992).

Primary Examiner—Chhaya D. Sayala
Attorney, Agent, or Firm—Lonnie R. Drayer

[57] ABSTRACT

A method of providing enteral nutritional support to a person who is currently undergoing chemotherapy and/or radiation therapy involves including in the person's diet an enteral nutritional product having a protein system which includes a soy protein hydrolysate. The nutritional product is very low in folic acid, contains β-carotene, and has a ratio of n-6 to n-3 fatty acids that is in the range of about 1.3:1 to 2.5:1.

19 Claims, No Drawings

METHOD OF PROVIDING ENTERAL NUTRITIONAL SUPPORT FOR PATIENTS UNDERGOING RADIATION THERAPY AND/OR CHEMOTHERAPY

The present invention relates to a method of providing enteral nutritional support for patients undergoing chemotherapy and/or radiotherapy.

Radiotherapy and/or chemotherapy are often used, for example, for the eradication of malignant cells present in the body, or for the treatment of other diseases. When one considers the example of abdominopelvic carcinomas treated with radiotherapy, pelvic radiation cannot kill malignant cells without causing some damage to the surrounding normal tissues. The normal tissue most often affected is the intestinal mucosa which, because of its rapidly dividing cells, is very radiosensitive. This same phenomenon also holds true for the use of chemotherapy in the eradication of malignant cells located throughout the body, or the treatment of other diseases, when treatment renders toxic trauma to the gastrointestinal tract. As an example, although chemotherapy is effective in targeting the malignant cells, or treating other diseases, its use is often associated with significant damage to normal nonmalignant cells, such as those which line the gastrointestinal tract. It is the failure to maintain homeostasis between cell depletion (induction of apoptosis) and cell proliferation (survival of pluripotent cells) with each successive dose of pelvic radiation and/or chemotherapy that results in the clinically observed acute gastrointestinal symptoms. Symptoms of both acute radiation/chemotherapy-induced damage represent the expression of radiation/chemotherapy-induced apoptosis and resultant functional changes in the bowel mucosa. Morphological changes as a result of pelvic radiation-and/or chemotherapy-induced apoptosis include, but are not limited to: (1) villi shortening; (2) reduction in total epithelial surface area; (3) reduction or disappearance of the glycocalyx and (4) loss of pluripotent cells.

Functional changes in the small bowel, induced by pelvic irradiation and/or chemotherapy include: malabsorption of fat, carbohydrate, protein, and bile salts, and clinically presents as diarrhea. Symptoms of nausea, vomiting and anorexia may also be experienced which results in a general nutritional wasting which is reversible. If these symptoms continue, weight loss, dehydration and severe nutrient losses occur. Symptoms of acute radiation/chemotherapy-induced enteritis usually abate shortly after the completion of treatment. The segment of the small intestine most affected by pelvic radiation is the ileum, and this is due to its pelvic position which puts it directly into the field of the radiation beam. The sigmoid colon could also be affected by pelvic radiation treatment due to its pelvic position.

The onset of chronic pelvic radiation injury may be delayed for months to years. Symptoms include intermittent bowel obstruction, fistulas, ulceration, perforation and generalized malabsorption. In the literature, there appears to be controversy over the natural history of chronic radiation-induced injury. Some report that an uneventful clinical course during and immediately after radiation does not provide a guarantee against the later development of malabsorption, obstruction, fistula or other complications. Others report that there appears to be no case of delayed enteropathy without a history of acute enteritis. Currently, there is no predictive test of late bowel damage. Medical management of late bowel damage is difficult and these late complications of radiation therapy can have an adverse effect on the host's nutrition status. The same scenario holds true for chronic chemotherapy-induced injury to the gastrointestinal tract.

The appropriate oral dietary interventions for clients with radiation/chemotherapy-induced enteritis are not well defined in the literature. Traditionally, low lactose, low roughage diets have been employed and may provide some relief of symptoms. Kouba, "Nutritional care of the individual with cancer", *Nutrition in Clinical Practice*, 3:175–182, 1988; Coulston, et al. "Nutrition management of patients with cancer", *Topics in Clinical Nutrition*, 12:26–36, 1986. More recently the use of elemental diets (chemically defined products that contain most nutrients in their simple molecular form) have been described as having an important role in preserving the morphological integrity of the gastrointestinal mucosa during radiation treatment. Bounous, "The use of elemental diets during cancer therapy", *Anticancer Research*, 3:299–304, 1983 If this can be confirmed, then acute and chronic radiation/chemotherapy-induced side effects could be minimized by the addition of an elemental diet throughout the course of pelvic radiation and/or chemotherapy treatment. Furthermore, nutritional support and symptom management may allow patients to more easily withstand treatment protocols, thus improving tumor control and overall patient prognosis and well-being.

Various animal models have been used to study the efficacy of elemental diets to protect against radiation/chemotherapy-induced bowel injury. Mice fed an elemental diet during single dose irradiation ranging from 700–1350 cGY were observed to have a better survival and less weight loss than mice eating regular diets. Hugon et al., "Elemental diet in the management of the intestinal lesions produced by radiation in the mouse", *Canadian Journal of Surgery* 15:18–26, 1972

McArdle et al., "Elemental Diet as Prophylaxis Against Radiation Injury", *ARCHIVES OF SURGERY*, Vol. 120, September 1985, pages 1026–1033 reports that feeding an elemental diet to dogs for three days before giving 2,000 rad of radiation afforded significant protection to the small intestine from the acute phase of radiation injury. The elemental diet employed in McArdle et al.'s study was VITAL® from Ross Laboratories, Columbus, Ohio, U.S.A. McArdle et al. later reported in "Prophylaxis Against Radiation Injury", *ARCHIVES OF SURGERY*, Vol. 121, August 1986, pages 879–884, that a study involving human patients suggested that elemental diet feeding provides prophylaxis against the acute phase of radiation injury in patients undergoing high doses, short-course radiotherapy for invasive bladder cancer and that it is a safe and feasible means of postoperative nutritional support, even in the presence of a fresh bowel anastomosis. The elemental diet employed in this study was also VITAL®.

A case report, Haddad et al., "Long term nutrition with an elemental diet following intensive abdominal radiation: Report of a case", *Diseases of the Colon and Rectum*, 17(3):373–375, 1974, investigated the long-term use of an elemental diet following intensive abdominal radiation in a woman diagnosed with ovarian cancer. Six weeks after abdominal radiation treatment with a total central pelvic dose of 4100 cGy followed by cGy to the whole pelvis, this woman experienced abdominal distention, abdominal pain, vomiting and weight loss. She was admitted to the hospital for nutritional support via nasogastric tube feedings. Upon discharge she continued to consume an oral elemental diet which was well tolerated. The patient's symptoms resolved and her nutritional status improved and was maintained with the elemental diet. Any attempts made to resume her original diet resulted in the resumption of her previous symptoms of diarrhea and nausea. The patient remained asymptomatic on the elemental diet. This case was the first report in which a chemically defined elemental diet was used exclusively for the long-term nutritional support of an adult patient experiencing acute radiation induced injury. Also, the return of symptoms on cross-over to the regular diet is compelling.

With this background, clinical trials were undertaken to investigate the possibility of protection against radiation enteropathy by the prophylactic administration of an elemental diet. A prospective study reported by Bounous et al., "Dietary protection during radiation therapy", *Strahlentherapie*, 149:476–483, 1975, alternatively assigned oncology patients undergoing pelvic or abdominal radiation treatment to receive either an elemental diet or a normal diet. Clinical outcome variables were weight change and diarrhea. Serum total protein and albumin levels were also measured. Results from this study indicated that subjects on the elemental diet were able to maintain weight and serum protein levels, whereas those in the control group lost weight and serum protein levels decreased. The elemental diet in the above study appeared to prevent radiation-induced diarrhea and to exert a favorable effect on the patients nutritional well-being. Radiation-induced diarrhea was a symptomatic problem experienced by 6 of the 9 subjects in the control group compared to only 1 of the 9 subjects in the elemental diet group. Furthermore, 3 of the 9 subjects in the control group required an interruption of radiation treatment because of an exacerbation of these symptoms. This interruption may ultimately affect tumor control and outcome. More importantly, it was evident that the patients in the study group were able to tolerate the oral administration of an elemental diet. It is reasonable to hypothesize from these observations that an elemental diet will result in fewer interruptions of radiation treatment, thus improving tumor control.

A more recent study, McArdle et al., "Prophylaxis against radiation injury", *Archives of Survey*, 121:879–884, 1986, investigated the use of an elemental diet in 20 patients undergoing radiation therapy of 2000 cGY over five days, prior to radical cystectomy and ileal conduit for invasive bladder cancer. These patients were supported for 7 days on an elemental diet either by nasogastric tube feeding or by oral administration. Initially, the research design called for the random allocation of patients to an elemental diet or to conventional nutrition management which consisted of either Total Parenteral Nutrition (TPN) or a regular hospital diet. A benefit of the elemental diet was observed early in the study and it was decided to discontinue other modes of nutritional support for ethical reasons. Hence, after the fourth elemental diet fed patient, the random allocation of patients was stopped and all patients were placed on an elemental diet and retrospective controls were used for comparison. The important clinical outcome of this study was the biopsy results of the terminal ileum taken at the time of surgery. All elemental diet fed patients showed no damage on histologic section. In contrast, moderate to severe radiation-induced damage was observed in the three consecutive patients who were not fed an elemental diet prior to radiation treatment.

In addition to the above studies, Bounous et al. have also demonstrated the beneficial effects of an elemental diet in patients undergoing chemotherapy with 5-fluorouracil (5-FU) Bounous et al., "Elemental diet in the management of the intestinal lesion produced by 5-fluorouracil in man", *Canadian Journal of Surgery*, 14, 1971, pages 312–324. In this study, twenty-four patients, 17 men and 7 women, with advanced metastatic carcinoma who were each receiving a standard dose of 5-FU, were randomly assigned to one of two experimental groups. The control group continued to consume the normal hospital diet throughout the nine day course of chemotherapy while the experimental group received an elemental diet as their sole source of nutrition during the same period. Patients in the control group eating a normal hospital diet, experienced significant weight loss and specific lesions of the rectal mucosa while patients on the experimental elemental diet had no rectal lesions and maintained their pretreatment body weight.

The effects of diet upon chemotherapy induced enterocolitis are also reported in Shou et al., "Dietary Manipulation of Methotrexate—Induced Enterocolitis", *JOURNAL OF PARENTERAL AND ENTERAL NUTRITION*, Vol. 15, No. 3, pages 307–312, 1991. The results of this study suggested that patients unable to ingest a regular diet while undergoing chemotherapy may benefit from a diet with polypeptides as a nitrogen source rather than an elemental diet. This publication advocates that elemental liquid diets cause changes in intestinal microflora characterized by a significantly increased level of Gram-negative bacteria. It is alleged that translocation of bacteria from the intestinal tract through the epithelial mucosa may cause infections that result at least in part from bacterial overgrowth, and that administration of certain elemental diets result in atrophy of the intestinal mucosa, with reduced mucosa villous height and crypt depth and other nondesirable results. It is important to note, however, that such detrimental results from an enteral diet have not been reported in any other publications.

As mentioned above, the underlying biological premise for clinically observable radiation-induced enteritis is the expression of programmed cell death (apoptosis) in both villus cells (non-dividing cells) and crypt cells (dividing pluripotent epithelial cells). The prevention of expression of such cell death would hypothetically translate into reduced clinically apparent enteritis, and may indeed further reduce or eliminate delayed onset enteritis. Moreover, the expectation of this reduction by an enteral formula may be based on the selection of ingredients which have been prescreened in a relevant tissue culture system for their inherent capacity to inhibit apoptosis. This basis, coupled with the above review of the literature, indicate that the use of such an elemental diet during pelvic radiation and/or chemotherapy treatment may have significant benefit to cancer patients undergoing treatment. Formulas selected by such means may reduce the morphological and functional changes in the intestinal mucosa associated with pelvic radiation and/or chemotherapy treatment. As a result, clinical morbidity may be minimized and nutritional status may be maintained. Furthermore, improvement in nutritional support and symptom control may allow patients to better withstand treatment protocols, which may subsequently improve tumor control.

In summary, the potential clinical benefits of an elemental diet during pelvic radiotherapy and/or chemotherapy are:

1. Reduction in radiation/chemotherapy-induced injury to the bowel mucosa (inhibition of apoptosis);
2. Reduction in the incidence and severity of bowel symptoms resulting from pelvic radiotherapy and/or chemotherapy;
3. Improved patient tolerance to pelvic radiation and/or chemotherapy; and
4. Assurance of a nutritionally adequate diet during treatment.

The present invention is a ready to feed, liquid enteral nutritional product designed specifically for the cancer patient undergoing radiation therapy and/or chemotherapy.

(Prior art elemental diets, such as Vital® have been marketed in a powdered form.) This product is specially designed to provide the gastrointestinal tract with a unique blend of nutrients which act to prophylactically block therapeutically-induced enteritis. This product can be utilized either as a nutritional supplement or as a sole source of nutrition and can be administered either orally or via tube feeding. This product is low in folic acid so as not to interfere with anti-folate chemotherapeutic therapies, is low in overall fat content so as not to promote diarrhea, and contains fermentable soluble fiber to provide essential nutrients to the large intestine. The specific features of this product include: (a) high caloric and nutrient density (1.3 kcal/ml); (b) a unique protein combination (SPH, whey, and pea proteins); (c) high omega-3 fatty acids; (d) fermentable soluble fiber; (e) reduced folic acid levels; (f) low fat; and (g) β-carotene fortification.

Protein is provided in one embodiment of the nutritional product of the present invention by a protein system which comprises, by weight:

(a) about 60% of a soy protein hydrolysate;

(b) about 30% of a whey protein concentrate; and (c) about 10% of a pea protein isolate.

However, in other embodiments of the present invention, the soy hydrolysate comprises by weight 60% to 90% of the protein system.

The soy protein hydrolyzate which is used as a source of protein in the nutritional product of the present invention may be manufactured using a process taught in U.S. Pat. No. 4,100,024, which is incorporated herein by reference for the purpose of teaching a process for manufacturing a soy protein hydrolysate for use in the nutritional product of the present invention. Briefly, this process for the preparation of polypeptides from soy protein soluble in aqueous media at pH's in the range of 2 to 7 involves: hydrolyzing soy protein with a microbial, alkaline proteinase in a concentration ranging from 4 to 25 Anson units per kg of soy protein at a substrate concentration of between 5 and 20% w/w soy protein, at a pH in the range of 7.5 to 8.5, until a degree of hydrolysis in the range of about 8 to 15% is attained, whereafter the enzyme is inactivated by reduction of pH with a food grade acid, the recovering the supernatant from the precipitate. However, it is understood that a soy protein hydrolyzate produced by any other process which has the characteristics elaborated upon herein may be used in the practice of the present invention.

An example of a nutritional product containing such a soy protein hydrolysate is taught in U.S. Pat. No. 4,959,350, but this prior art nutritional product has a pH of lower than 4.5 (as compared to a pH of 6.3 to 6.6 in the product of the present invention) and has an osmolality of below about 350 mosm/kg water (as compared to about 600 mosm/kg water in the nutritional product of the present invention). This prior art nutritional product may be further distinguished from the nutritional product of the present invention by the fat composition, fiber content, and vitamin and mineral profiles of the product of the present invention.

The nutritional product of the present invention has been manufactured using soy protein hydrolysate obtained from NOVO Industri A/S, Bagsvaerd, Denmark, manufactured according to the above described process. The properties of a soy protein hydrolysate which is suitable for use in the practice of the present invention have been determined by actual analysis of samples from several lots of soy protein hydrolysate obtained from NOVO Industri and/or specifications selected in accordance with desired properties.

It is believed to be very important that the soy protein hydrolysate used in the practice of the invention comprise, by weight, not less than 76%, preferably not less than 80% protein, not more than 1% fat, and not more than 5.5%, preferably not more than 4.8% ash. It is also believed to be very important that a 5% slurry (by weight) of the soy protein hydrolysate in water has a pH in the range of about 4.2 to 4.3, but in any instance less than 4.5. It is believed to be important that the degree of hydrolysis of the soy protein hydrolysate (AN/TN×100) be in the range of about 14 to 17% and most preferably about 16%.

The amino acid profile of the soy protein hydrolysate that has been used in the practice of the present invention is presented in Table 1, and the mineral profile is presented in Table 2. The molecular weight profile is presented in Table 3 for soy protein hydrolysate (SPH) having about a 16% degree of hydrolysis with the approximate molecular weight partition determined by size exclusion chromatography of samples from 4 lots of SPH. The molecular weight profile of the soy protein hydrolysate is believed to be very important because particles sizes are related to their physical activity and product functionality. That is to say, for the SPH used in the nutritional product of the present invention the molecular weight profile indicates a large peptide content and a small free amino acid content of less than 1%. The mineral profile of the soy protein hydrolysate is believed to be very important because it supplies most of the trace and ultratrace minerals in the nutritional product.

TABLE 1

AMINO ACID PROFILE OF SOY PROTEIN HYDROLYSATE (g/100 g)

| | |
|---|---|
| Aspartic acid | 9.8–10.4 |
| Threonine | 2.9–3.2 |
| Serine | 3.7–4.4 |
| Glutamic Acid | 17.0–18.1 |
| Proline | 4.4–4.9 |
| Glycine | 3.2–3.3 |
| Alanine | 3.0–3.2 |
| Valine | 2.9–3.6 |
| Methionine | 0.9–1.1 |
| Isoleucine | 3.0–3.7 |
| Leucine | 5.1–5.3 |
| Tyrosine | 2.7–2.9 |
| Phenylalanine | 3.3–3.5 |
| Histidine | 2.0–2.2 |
| Lysine | 5.5–5.8 |
| Arginine | 6.3–6.7 |
| Tryptophan | 0.3–0.7 |
| Cystine | 1.3–1.4 |

TABLE 2

MINERAL PROFILE OF SOY PROTEIN HYDROLYSATE

| | Preferred Range | Most Preferred Range |
|---|---|---|
| Calcium, mg/100 g | 170–350 | 170–260 |
| Sodium, mg/100 g | 370–650 | 370–520 |
| Potassium, mg/100 g | 180–600 | 180–470 |
| Magnesium, mg/100 g | 270–550 | 270–400 |
| Phosphorus, mg/100 g | 900–1500 | 900–1200 |
| Chloride, mg/100 g | 1400–2500 | 1400–2250 |
| Iron, mg/100 g | 13–25 | 13–20 |
| Zinc, mg/100 g | 3–6 | 3–6 |
| Manganese, mg/100 g | 4–8 | 5–7 |
| Copper, mg/100 g | 0.5–1.5 | 0.5–1.0 |
| Vanadium, ppm | trace–15 | 8–12 |
| Selenium, ppb | trace–350 | 150–300 |
| Chromium, ppm | trace–2.9 | 1.5–2.3 |
| Molybdenum, ppm | trace–3.7 | 2–3 |

TABLE 3

MOLECULAR WEIGHT PARTITION FOR SPH
(AS DETERMINED BY SIZE EXCLUSION
CHROMATOGRAPHY OF SAMPLES FROM FOUR
DIFFERENT LOTS OF SPH)

| | % of Particles With This Molecular Wt. | | |
|---|---|---|---|
| Molecular Wt. | Average | Std. Deviation | Range |
| >5000 | 3.3 | 1.96 | 1.70–5.96 |
| 2000–5000 | 25.8 | 5.42 | 19.50–30.75 |
| 1500–2000 | 20.5 | 7.41 | 13.10–27.50 |
| 1200–1500 | 12.5 | 0.92 | 11.80–13.80 |
| 1000–1200 | 8.2 | 0.83 | 7.30–9.00 |
| 500–1000 | 19.5 | 3.02 | 16.80–23.80 |
| <500 | 10.2 | 6.03 | 5.30–19.00 |

It was discovered that the soy protein hydrolyzate used in the nutritional product of the present invention does not yield a shelf stable product in the absence of intact protein. Once a protein is hydrolyzed, it loses its primary and secondary structure and consequently some of its functionality, including emulsifying properties. Therefore, it does not have surfactant properties and is unable to stabilize the formulation resulting in phase separation. Various approaches were investigated to attempt to stabilize a liquid product containing this particular soy protein hydrolyzate. Three different emulsifiers, and combinations thereof, were evaluated, but the most effective emulsifier is Panodan® which is distributed by GRINSTED of Danisco, Denmark. Panodan® is diacetyl tartaric acid esters of mono-diglycerides and is an anionic surfactant with a very hydrophilic component attached. Panodan® is generally regarded as safe (GRAS) for use in nutritional products for human consumption. Panodan® works by imparting a negative charge to the fat globules, thus, causing them to electrostatically repel each other so that no flocculation or coalescence occurs. The soy protein hydrolysate could stay in an emulsion for about two weeks with Panodan® and no other protein source present It is, however, believed that sodium stearolyl lactylate could also be used as an emulsifier, but this emulsifier has not yet been classified as GRAS by the U.S. Food and Drug Administration. It is believed that a product in accordance with the present invention maybe manufactured without an emulsifier if the content of intact protein is great enough.

The sources of intact protein selected for use in the product of the present invention are pea protein isolate and whey protein concentrate. One of the advantages of using pea protein and whey protein is that it helps to alleviate the bitter taste of the product. Caution must be taken not to use too much pea protein or the viscosity of the product may be too high. It is to be understood that the component(s) of the protein system of a nutritional product of the present invention comprising intact protein could comprise any suitable source of intact protein, such as sodium caseinate, whether in place of or in addition to the pea protein and whey protein used in the preferred embodiment.

An important feature of the nutritional product of the present invention is the inclusion of pea protein isolate as a source of protein. Product has been manufactured using PISANE® PEA PROTEIN ISOLATE distributed by Cosucra SA of Momalle, Belgium. This commercially available pea protein isolate is a cream colored powder of particles having sizes of smaller than about 150 microns. Per the distributor's sales literature on a dry weight basis the pea protein isolate is: a minimum of 88% protein, a maximum of 0.2% fat, about 5% ash, and the pH of a 10% aqueous solution of the protein isolate is about 7.5. Per the distributor's sales literature functional properties of the pea protein isolate are: 60% minimum solubility at pH 7, 15% minimum solubility at pH 4.5, and 90% minimum emulsion stability (O/W =40/60, 1% PISANE®, pH 3 to 7). Table 4 presents the average amino acids content of the pea protein isolate per the distributor's sales literature.

TABLE 4

AMINO ACIDS CONTENT OF PEA PROTEIN ISOLATE
(g/100 g protein)

| Glycine | 4.3 |
|---|---|
| Alanine | 20.7 |
| Valine | 3.7 |
| Leucine | 7.7 |
| Isoleucine | 3.1 |
| Serine | 5.2 |
| Threonine | 3.8 |
| Tyrosine | 3.5 |
| Aspartic acid | 11.8 |
| Phenylalanine | 5.0 |
| Tryptophan | 1.0 |
| Proline | 4.4 |
| Methionine | 1.0 |
| Cysteine | 1.4 |
| Lysine | 7.5 |
| Histidine | 2.2 |
| Arginine | 7.7 |
| Glutamic acid | 20.7 |

The Bill of Materials for manufacturing a 1,000 pound batch of a nutritional product in accordance with the present invention is presented in Table 5. It is to be understood that this Bill of Materials is only an example for one flavor that has been manufactured and that functionally equivalent ingredients may be substituted into the Bill of Materials without deviating from the scope of the invention.

TABLE 5

BILL OF MATERIALS

| INGREDIENT | AMOUNT 454 Kg (1,000 LB) BATCH | |
|---|---|---|
| Medium Chain Triglycerides (MCT) Oil | 1.785 kg | (3.932 lbs) |
| Canola Oil | 5.081 kg | (12.779 lbs) |
| Panodan ® (emulsifier) | 445.880 gms | |
| Oil Soluble Vitamin Premix: | 24.140 gms | |
| Vitamin A | 1.683 gms | |
| Vitamin D | 0.159 gms | |
| Vitamin E | 17.319 gms | |
| Vitamin K | 0.033 gms | |
| Vitamin A | 0.382 gms | |
| β-Carotene | 8.935 gms | |
| Iota Carrageenan | 68.040 gms | |
| Gum Arabic | 3.822 kg | (8.418 lbs) |
| Fish Oil | 0.892 kg | (1.966 lbs) |
| Water | 315.899 kg | (694.970 lbs) |
| Whey Protein Concentrate | 11.670 kg | (25.770 lbs) |
| Sodium Citrate | 1.724 kg | (3.797 lbs) |
| Magnesium Phosphate* | 527.970 gms | |
| Calcium Carbonate | 465.470 gms | |
| Calcium Phosphate* | 447.060 gm | |
| Maltrin ® 040 (maltodextrin) | 71.491 kg | (157.470 lbs) |
| Sucrose | 11.986 kg | (26.400 lbs) |
| Soy Protein Hydrolysate | 19.931 kg | (43.900 lbs) |
| Potassium Hydroxide 45% | 3.094 kg | (6.806 lbs) |
| Pea Protein Isolate | 3.234 kg | (7.120 lbs) |
| Zinc Sulfate | 8.628 gms | |
| Copper Sulfate | 1.717 gms | |
| Sodium Selenate | 0.039 gms | |
| Ascorbic Acid | 412.364 gms | |
| Choline Chloride | 41.667 gms | |

TABLE 5-continued

BILL OF MATERIALS

| INGREDIENT | AMOUNT 454 Kg (1,000 LB) BATCH | |
| --- | --- | --- |
| Carnitine | 35.000 gms | |
| Taurine | 49.484 gms | |
| Niacinamide | 7.635 gms | |
| d-Ca Calcium Pantothenate | 4.885 gms | |
| Folic Acid | 0.064 gms | |
| Thiamine HCl | 1.186 gms | |
| Riboflavin | 1.010 gms | |
| Pyridoxine HCl | 1.228 gms | |
| Cyanocobalamin | 0.003 gms | |
| Biotin | 0.153 gms | |
| Artificial Vanilla | 1.135 kg | (2.500 lbs) |
| Natural and Artificial Vanilla | 0.909 kg | (2.000 lbs) |

*Phosphorus content may need to be adjusted i view of phytate content of the SPH.

The nutritional product of the present invention may be manufactured using the ingredients from the above Bill of Materials by: (a) preparing several slurries/solutions which are then combined together; (b) heat processing the resultant blend; (c) adding vitamins, minerals and flavorings; and (d) packaging and sterilizing the resultant product.

An oil blend is prepared by the following procedure. The medium chain triglycerides and canola oil are placed in a vessel and while being continuously agitated are heated to a temperature in the range of about 60°– 65° C. (140°–150° F.). The product has been manufactured using fractionated coconut oil as the source of MCT, but any other suitable source of MCT may be used. Add the Panodan® (an emulsifier) to the resultant oil blend and allow it to dissolve therein before adding the remaining ingredients. Panodan distributed by Grinsted of Danisco, Denmark, (which also has a distributor located in Kansas, U.S.A.) is a diacetyl tartaric acid ester of mono-diglycerides, made from edible refried vegetable fat. Add the oil soluble vitamin premix, vitamin A, and β-carotene to the oil blend. Combine the iota carrageenan with the gum arabic, and add this mixture to the oil blend. Cool the oil blend to a temperature in the range of about 43°–49° C. (110°–120° F.). Add the fish oil to the oil blend, and maintain the oil blend at a temperature of about 43°–49° C. (110°–120° F.) under constant agitation until the oil blend is combined with other ingredients. The product has been manufactured using marine oil made from tuna and sardine meal, distributed by Mochida International of Shinjuku-ku, Tokyo, Japan, but is produced and packaged by the Sambugun, Chiba plant of the Kyowa Technos Co., Ltd.

A protein-in-water slurry is prepared by the following procedure. About 95.79 kg (210.74 pounds) of water is placed in a vessel and heated to a temperature in the range of about 54°–60° C. (130°–140° F.). It is believed to be critical that the temperature of the water does not exceed 60° C. (140° F.) during this procedure. Add the pea protein isolate and then the whey protein concentrate to the water, and maintain the resultant protein-in-water slurry under agitation at a temperature of about 54° C. (130° F.) until this slurry is combined with other ingredients. The resultant slurry is about 13.5% total solids.

A carbohydrate slurry is prepared by the following procedure. About 130.41 kg (286.9 pounds) of water is placed in a vessel and heated to a temperature in the range of about 68°–74° C. (155°–165° F.). Dissolve the sodium citrate, magnesium phosphate, calcium carbonate, and calcium phosphate in the water. To the resultant solution add the Maltrin® 040 (distributed by Grain Processing Company of Muscatine, Iowa, U.S.A.) and agitate the solution until the Maltrin® 040 is dissolved therein. Maltrin® 040 is a maltodextrin, or corn syrup solid. The number 40 refers to the dextrose equivalent of the ingredient (4 to 7) and was selected to minimize the effect of this ingredient on the osmolality of the nutritional product. To the resultant solution add the sucrose and the soy protein hydrolysate. The resultant slurry should have a pH of about 4.3. Add 3.09 kg (6.806 lbs) of 45% potassium hydroxide to the slurry in an amount sufficient to adjust the pH of the slurry to be in the range of about 6.3–6.5. (If necessary the amount of 45% potassium hydroxide may exceed the amount specified). The slurry is maintained at a temperature in the range of about 54°–60° C. (130°– 140° F.) under agitation until the slurry is combined with other ingredients. The resultant slurry is about 45% of total solids prior to the addition of the potassium hydroxide.

The oil blend, carbohydrate slurry, and first and second protein-in-water slurries are all combined together. The resultant final blend is then heat processed by the following procedure:

(a) The final blend is preheated to a temperature in the range of about 68°–74° C. (155°–165° F.).

(b) The final blend is de-aerated at 13–15 psi.

(c) The final blend is emulsified at 900–1100 psig.

(d) The final blend is heated to a temperature in the range of about 98°–106° C. (208°–222° F.) using a plate heater.

(e) The final blend is then heated to a ultra-high temperature in the range of about 146°–147° C. (294°–297° F.), and is held at this temperature for 5 seconds.

(f) The final blend is then flash cooled to a temperature in the range of about 98°–106° C. (208°–222° F.), then plate cooled to a temperature in the 71°–79° C. (160°–175° F.).

(g) The final blend is homogenized at 3900–4100/ 400–600 psig.

(h) The final blend is held at a temperature in the range of about 74°–85° C. (165°–185° F.) for 16 seconds.

(i) The final blend is then cooled to a temperature in the range of about 1°–7° C. (34°–45° F.), and held at this temperature until the product is sealed in containers (preferably within 48 hours).

An ultra trace mineral solution is prepared by the following procedure. About 93.89 gm (0.207 pounds) of water are placed in a vessel and heated to a temperature in the range of about 66°–71° C. (150°–160° F.). The zinc sulfate, copper sulfate and sodium selenate are then added to the water and the solution is agitated until these ingredients dissolve in the water. The resultant solution is about 10% total solids. The resultant solution is then added to the final blend.

A water soluble vitamin solution is then prepared by the following procedure. About 2.89 kg (6.366 pounds) of room temperature water is placed in a vessel. The ascorbic acid, 45% potassium hydroxide (00284.4 gm (0.627 lbs), choline chloride, carnitine, and taurine are added to the water with agitation. To the resultant solution the following vitamins are added: niacinamide, d-calcium pantothenate, folic acid, thiamine HCl, riboflavin, pyridoxine HCl, cyancobalamin, and biotin. The resultant solution is about 20% total solids. The resultant solution is then added to the final blend. It is understood that in large scale production it would be preferable to have the water soluble vitamins provided in a premix.

A flavor solution is then prepared by the following procedure. About 86.71 kg (190.757 pounds) of room temperature water is placed in a vessel. The artificial vanilla and the natural and artificial vanilla are dissolved in the water. The resultant solution is about 5% of total solids. The flavor solution is then added to the final blend. The resultant final blend is about 29% total solids.

The final blend is then placed in suitable containers, such as 8 ounce cans, sealed with a suitable closure, and subjected to terminal sterilization.

The nutrient profile of a nutritional product in accordance with the invention is presented in Table 6. The amino acid profile of the new nutritional product is presented in Table 7, and the fatty acid profile of the new nutritional product is presented in Table 8.

TABLE 6

NUTRIENT PROFILE OF PRODUCT

| | TARGET | ACCEPTABLE RANGE | |
|---|---|---|---|
| | (per 8 fluid oz.) | (per 8 fluid oz. can) | per liter |
| Total Solids | 75.64 | 73.3–78.0 | 309.7–329.6 |
| Protein, g | 15.83 | 15.4–16.3 | 65.1–68.9 |
| 60% Soy Protein Hydrolyzate | | | |
| 30% Whey Protein Concentrate | | | |
| 10% Pea Protein Isolate | | | |
| Fat, g | 5.43 | 5.2–6.1 | 22.0–26.0 |
| 65% Canola Oil | | | |
| 20% MCT Oil | | | |
| 10% Fish Oil | | | |
| 5% Panodan (emulsifier) | | | |
| Carbohydrate, g | 46.80 | 44.9–49.6 | 189.7–209.6 |
| 85% Maltrin ® 040 | | | |
| 15% Sucrose | | | |
| Fiber (Gum Arabic), g | 1.90 | 1.4–2.5 | 5.9–10.5 |
| Water Soluble Vitamins | | | |
| Vitamin C, mg | 189 | 151–236 | 640–1000 |
| Folic Acid, mcg | 36.6 | 33.0–42.5 | 139.4–179.6 |
| Thiamine, mg | 0.66 | 0.59–0.90 | 2.49–3.80 |
| Riboflavin, mg | 0.57 | 0.49–0.71 | 2.07–3.00 |
| Pyridoxine, mg | 0.6 | 0.4–0.7 | 2.0–2.8 |
| Cyancobalamin, mcg | 1.73 | 1.55–2.36 | 6.6–9.5 |
| Niacin, mg | 4.3 | 3.7–5.9 | 15.6–24.9 |
| Choline, mg | 34.3 | 30.7–37.8 | 129.7–159.7 |
| Biotin, mcg | 87.5 | 77.9–96.9 | 329.1–409.4 |
| Pantothenic Acid, mg | 2.4 | 2.1–4.7 | 9.0–17.5 |
| Oil Soluble Vitamins | | | |
| Vitamin A, IU | 1198 | 1063–1654 | 4491–6988 |
| Vitamin D, IU | 91 | 82–100 | 346–422 |
| Vitamin E, IU | 9.9 | 8.5–10.9 | 35.9–46.0 |
| Vitamin K, mcg | 18.9 | 16.5–24.6 | 69.7–104.0 |
| β-Carotene, mcg | 945 | 709–1418 | 2995–5948 |
| Minerals | | | |
| Calcium, mg | 234 | 195–273 | 825–1155 |
| Sodium, mg | 320 | 283–354 | 1196–1496 |
| Potassium, mg | 475 | 449–567 | 1897–2396 |
| Magnesium, mg | 100 | 89–118 | 376–498 |
| Phosphorus, mg | 296 | 260–338 | 1100–1430 |
| Chloride, mg | 350 | 330–378 | 1394–1597 |
| Molybdenum, mcg | 63.8 | 16–106 | 67–448 |
| Iodine, mcg | 21.3 | 18.9–37.2 | 79.8–157.5 |
| Manganese, mcg | 0.9 | 0.7–1.2 | 3.0–5.1 |
| Copper, mg | 0.5 | 0.2–0.7 | 0.8–3.0 |
| Zinc, mg | 2.4 | 1.1–3.5 | 4.6–14.8 |
| Iron, mg | 3.5 | 2.8–3.5 | 11.8–14.8 |
| Selenium, mcg | 17.7 | 11.8–23.6 | 49.9–99.7 |
| Chromium, mcg | 33.1 | 11.8–47.3 | 49.9–199.8 |
| Carnitine, mg | 20.1 | 17.7–26.0 | 74.8–109.8 |
| Taurine, mg | 28.4 | 14.1–30.7 | 59.6–129.7 |

TABLE 7

AMINO ACID PROFILE OF PRODUCT

| AMINO ACID | g/100 g sample |
|---|---|
| Aspartic Acid | 0.753 |
| *Threonine | 0.307 |
| Serine | 0.339 |
| Glutamic Acid | 1.231 |
| Proline | 0.351 |
| Glycine | 0.221 |
| Alanine | 0.275 |
| *Valine | 0.274 |
| *Methionine | 0.092 |
| *Isoleucine | 0.290 |
| *Leucine | 0.503 |
| Tyrosine | 0.205 |
| *Phenylalanine | 0.276 |
| Histidine | 0.153 |
| *Lysine | 0.480 |
| Arginine | 0.391 |
| *Tryptophan | 0.062 |
| Cystine | 0.105 |
| TOTAL | 6.307 |

*Essential amino acid

TABLE 8

FATTY ACID PROFILE OF PRODUCT

| FATTY ACID | % of TOTAL FATTY ACIDS |
|---|---|
| Caprylic (8:0) | 12.5 |
| Capric (10:0) | 8.9 |
| Lauric (12:0) | 0.4 |
| Myristic (14:0) | 1.1 |
| Palmic (16:0) | 5.3 |
| Palmitoleic (16:1n7) | 1.0 |
| Stearic (18:0) | 3.8 |
| Oleic (18:1n9) | 39.1 |
| Linoleic (18:2n6) | 14.2 |
| Alpha-Linolenic-(18:3n3) | 6.0 |
| Stearidonic (18:4n3) | 0.4 |
| Arachidic (20:0) | 0.4 |
| Eicosenoic (20:1n9) | 1.0 |
| Arachidonic (20:4n6) | 0.2 |
| Eicosapentaenoic (20:5n3) | 2.9 |
| Erucic (22:1n9) | 0.4 |
| Docsapentaenoic (22:5n3) | 0.3 |
| Docosahexaenoic (22:6n3) | 1.3 |
| Others | 0.6 |

The enteral nutritional product of the present invention is characterized by the ratio, by weight, of the sum of the n-6 fatty acids to the sum of the n-3 fatty acids being in the range of about 1.3:1 to 2.5:1.

The nutritional product of the present invention is low in folic acid content because folic acid competes with some of the drugs used in cancer therapy for dihydrofolate reductase enzyme and methyl transfer.

The nutritional product of the present invention contains β-carotene, carnitine and taurine. β-carotene is a carotenoid compound that has pro vitamin A activity. However, unlike vitamin A, β-carotene is not associated with toxicity and, therefore, may be used as a source of retinol equivalents in the diet without inducing toxicity concerns. Vitamin A has been shown to reverse some of the immunosuppression associated with thermal injury and radiation injury. Favorable effects on the immune system also have been observed with β-carotene supplementation.

Although carnitine and taurine are present in low but adequate levels in a normal diet, these conditionally essential nutrients may become limiting under some circumstances. Carnitine deficiency has been observed in sepsis and trauma and during long-term enteral nutrition support. Evidence of taurine depletion has been demonstrated after surgical trauma and a decline in serum taurine concentrations during metabolic stress suggests that taurine supplementation is needed in that state. In humans intensive cytoxic chemotherapy is known to reduce taurine levels.

As used herein and in the claims "dietary fiber" and/or "total dietary fiber" is understood to mean plant material that is undigested by human alimentary enzymes. Dietary fiber is known to be beneficial in regulating bowel function in diarrhea. Inclusion of dietary fiber in the diet also stimulates the renewal of intestinal epithelial cells and mucosal growth. The nutritional product of the present invention contains fermentable soluble dietary fiber in the form of gum arabic.

The enteral nutritional product of the present invention is formulated to be used as a sole source of nutrition over a relatively short period of time: for example, starting a few days before this initiation of chemotherapy and/or radiation therapy, during the therapy period, and stopping two or three days after the completion of the therapy period. Feeding of this new enteral nutritional product over a longer period of time will result in a decrease in the beneficial response to the nutritional product. Preferably, during periods between the administration of chemotherapy and/or radiation therapy the patient will consume a normal healthy diet. If it is necessary to supplement the patient's diet during periods between the administration of chemotherapy and/or radiation therapy a nutritional supplement of the type disclosed in commonly assigned U.S. patent application Ser. No. 08/069,067 filed May 28, 1993.

We claim:

1. A method of providing enteral nutritional support for a person undergoing radiation therapy and/or chemotherapy by including in said person's diet a liquid enteral nutritional product comprising:
   (a) a soy protein hydrolysate having a molecular weight partition, as determined by size exclusion chromatography, wherein 30–60% of the particles have a molecular weight in the range of 1,500–5,000 Daltons, the soy protein hydrolysate provides by weight 60% to 90% of the protein in the nutritional product;
   (b) a second source of protein which comprises a source of intact protein in a quantity sufficient to yield a stable emulsification of the soy protein hydrolysate and the intact protein in the nutritional product, the intact protein comprising by weight at least 10% of the protein in the nutritional product, said second source of protein comprising pea protein;
   (c) a source of fat characterized by the ratio, by weight, of the sum of the n-6 fatty acids to the sum of the n-3 fatty acids being in the range of about 1.3:1 to 2.5:1; said nutritional product being terminally sterilized and have a pH of about 6.3–6.6.

2. A method of providing enteral nutritional support according to claim 1 wherein the source of intact protein in the nutritional product is a combination of pea protein and whey protein.

3. A method of providing enteral nutritional support according to claim 2 wherein the nutritional product further comprises gum arabic.

4. A method of providing enteral nutritional support according to claim 1 wherein the nutritional product further comprises a source of dietary fiber.

5. A method of providing enteral nutritional support according to claim 1 wherein the nutritional product has a fat content of 22 to 26 g of fat per liter.

6. A method of providing enteral nutritional support according to claim 1 wherein the nutritional product further comprises about 2,995 to 5,948 mcg per liter of β-carotene.

7. A method of providing enteral nutritional support for a person undergoing radiation therapy and/or chemotherapy by including in said person's diet a liquid enteral nutritional product comprising:
   (a) a first source of protein comprising a soy protein hydrolysate having a degree of hydrolysis in the range of about 14 to 17% and a molecular weight partition, as determined by size exclusion chromatography, wherein 30–60% of the particles have a molecular weight in the range of 1,500–5,000 Daltons, the soy protein hydrolysate provides by weight 60% to 90% of the protein in the nutritional product;
   (b) a second source of protein comprising a combination of intact pea protein and intact whey protein, the intact proteins comprising in combination by weight at least 10% of the protein in the nutritional product; and
   (c) a source of fat characterized by the ratio, by weight, of the sum of the n-6 fatty acids to the sum of the n-3 fatty acids being in the range of about 1.3:1 to 2.5:1; said nutritional product being terminally sterilized and having a pH of about 6.3–6.6.

8. A method of providing enteral nutritional support according to claim 7 wherein the nutritional product further comprises about 2,995 to 5,948 mcg per liter of β-carotene.

9. A method of providing enteral nutritional support according to claim 8 wherein the nutritional product further comprises gum arabic.

10. A method of providing enteral nutritional support according to claim 7 wherein the nutritional product further comprises a source of dietary fiber.

11. A method of providing enteral nutritional support according to claim 10 wherein the nutritional product has a fat content of 22 to 26 g of fat per liter.

12. A method of providing enteral nutritional support according to claim 7 wherein the nutritional product further comprises gum arabic.

13. A method of providing enteral nutritional support according to claim 12 wherein the nutritional product has a fat content of 22 to 26 g of fat per liter.

14. A method of providing enteral nutritional support according to claim 7 wherein the nutritional product has a fat content of 22 to 26 g of fat per liter.

15. A method of providing enteral nutritional support according to claim 7 wherein the nutritional product has a protein source comprising by weight about 60% of said soy protein hydrolysate, about 30% of said whey protein, and about 10% of said pea protein.

16. A method of providing enteral nutritional support for a person undergoing radiation therapy and/or chemotherapy by including in said person's diet a liquid enteral nutritional product comprising:
   (a) a first source of protein comprising a soy protein hydrolysate having a degree of hydrolysis in the range of about 14 to 17% and a molecular weight partition, as determined by size exclusion chromatography, wherein 30 to 60% of the particles have a molecular weight in the range of 1,500–5,000 Daltons said soy protein hydrolysate provides, by weight about 60% of the protein in said nutritional product;
   (b) a second source of protein comprising intact whey protein concentrate, said whey protein concentrate comprising, by weight, about 30% of the protein in said nutritional product;

(c) a third source of protein comprising intact pea protein isolate, said pea protein isolate comprising, by weight, about 10% of the protein in said nutritional product;

(d) a source of diacetyl acid esters of mono-diglycerides;

(e) a fat blend comprising fish oil and at least one other source of fat, said fat blend characterized by the ratio, by weight, of the sum of the n-6 fatty acids to the sum of the n-3 fatty acids being in the range of about 1.3:1 to 2.5:1; said nutritional product being terminally sterilized and having a pH of about 6.3–6.6.

17. A method of providing enteral nutritional support according to claim 16 wherein the nutritional product further comprises gum arabic.

18. A method of providing enteral nutritional support according to claim 16 wherein the nutritional product further comprises about 2,995 to 5,948 mcg per liter of β-carotene.

19. A method of providing enteral nutritional support according to claim 16 wherein the nutritional product has a fat content of 22 to 26 g of fat per liter.

* * * * *